US012805621B2

(12) United States Patent
Suthiwangcharoen et al.

(10) Patent No.: US 12,805,621 B2
(45) **Date of Patent: *Nov. 24, 2026**

(54) PROCESS FOR REDUCING HAIR DAMAGE UPON EXPOSURE TO HEAT

(71) Applicants: Dow Global Technologies LLC, Midland, MI (US); Rohm and Haas Company, Collegeville, PA (US); Dow Silicones Corporation, Midland, MI (US)

(72) Inventors: Nisaraporn Suthiwangcharoen, Midland, MI (US); Lyndsay M. Leal, Spring City, PA (US); Emmett M. Partain, III, Bound Brook, NJ (US); Shannon Golden, Saginaw, MI (US); Justin Scherzer, Freeland, MI (US); Kenneth L Kearns, Jr., Midland, MI (US)

(73) Assignees: DOW GLOBAL TECHNOLOGIES LLC, Midland, MI (US); ROHM AND HAAS COMPANY, Collegeville, PA (US); DOW SILICONES CORPORATION, Midland, MI (US)

( * ) Notice: Subject to any disclaimer, the term of this patent is extended or adjusted under 35 U.S.C. 154(b) by 804 days.

This patent is subject to a terminal disclaimer.

(21) Appl. No.: 17/918,251

(22) PCT Filed: May 27, 2021

(86) PCT No.: PCT/US2021/034382

§ 371 (c)(1),
(2) Date: Oct. 11, 2022

(87) PCT Pub. No.: WO2021/242942

PCT Pub. Date: Dec. 2, 2021

(65) Prior Publication Data

US 2023/0145339 A1 May 11, 2023

Related U.S. Application Data

(60) Provisional application No. 63/031,699, filed on May 29, 2020.

(51) Int. Cl.

| | |
|---|---|
| ***A45D 19/00*** | (2006.01) |
| ***A61K 8/41*** | (2006.01) |
| ***A61K 8/73*** | (2006.01) |
| ***A61Q 5/00*** | (2006.01) |
| ***A61Q 5/12*** | (2006.01) |

(52) U.S. Cl.

CPC .......... *A45D 19/0041* (2021.01); *A61K 8/731* (2013.01); *A61Q 5/00* (2013.01); *A61K 2800/48* (2013.01)

(58) Field of Classification Search

CPC ................ A45D 19/0041; A61K 8/731; A61K 2800/48; A61K 8/416; A61K 2800/5426; A61Q 5/00; A61Q 5/12

See application file for complete search history.

(56) References Cited

U.S. PATENT DOCUMENTS

| | | | |
|---|---|---|---|
| 6,380,336 | B1 | 4/2002 | Soane |
| 6,465,419 | B1 | 10/2002 | Oses et al. |
| 6,486,105 | B1 | 11/2002 | Cannell et al. |
| 7,138,366 | B2 | 11/2006 | Grandmaire et al. |
| 7,718,597 | B2 | 5/2010 | Grainger et al. |
| 8,138,134 | B2 | 3/2012 | Zhang et al. |
| 8,771,658 | B2 | 7/2014 | Humphreys et al. |
| 8,790,627 | B2 | 7/2014 | Erazo-Majewicz et al. |
| 8,889,610 | B2 | 11/2014 | Labeque et al. |
| 9,427,603 | B2 | 8/2016 | Seng, Sr. et al. |
| 10,377,967 | B2 | 8/2019 | Schymitzek et al. |
| 11,246,821 | B2 | 2/2022 | Davis et al. |
| 2002/0172653 | A1 | 11/2002 | Cannell et al. |
| 2002/0175310 | A1 | 11/2002 | Messner et al. |
| 2004/0115155 | A1 | 6/2004 | Salvador et al. |

(Continued)

FOREIGN PATENT DOCUMENTS

| | | |
|---|---|---|
| CN | 1259860 | 7/2000 |
| EP | 3441449 | 2/2019 |

(Continued)

OTHER PUBLICATIONS

Daltosur, JR-400 polyquaternium-10, [Retrieved on Dec. 2, 2025], Retrieved online, Weblink <https://daltosur.com/media/documents/ucare-polymer-jr-400tds062022.pdf> [2018-2021

Sibilia, "A Guide to Materials Characterization and Chemical Analysis", VCH, 1988, pp. 81-84.

Yau, "Gel Permeation Chromatography", Modern Size Exclusion Chromatography, Wiley-Interscience, 1979, pp. 81-84.

Zhou, "The effect of various cosmetic pretreatments on protecting hair from thermal damage by hot flat ironing", J. Cosmet Sci, 2011, vol. 62, pp. 265?282. ] (Year: 2021).*

*Primary Examiner* — Sue X Liu
*Assistant Examiner* — Dongxiu Zhang
(74) *Attorney, Agent, or Firm* — CANTOR COLBURN LLP

(57) ABSTRACT

A process for reducing hair damage upon exposure to heat is provided, including: providing aqueous carrier; selecting heat protectant, wherein heat protectant is selected for its ability to impart thermal protection to hair and to be modified carbohydrate polymer, comprising cellulose ether base material functionalized with trialkyl ammonium moieties, having Kjeldahl nitrogen content of 0.75 to 2.5 wt %; and hydrophobic substituents having 16 carbon atoms; providing the selected heat protectant; combining the cosmetically acceptable aqueous carrier and the heat protectant to form aqueous thermal protectant formulation; wherein the aqueous thermal protectant formulation contains 0.1 to 5 wt %, based on weight of the aqueous thermal protectant formulation, of the heat protectant; providing hair; applying the aqueous thermal protectant formulation to hair; providing heat generating hair care appliance; exposing hair to heat at 50 to 300 °C using the heat generating hair care appliance for 1 to 30 minutes.

15 Claims, No Drawings

(56) References Cited

U.S. PATENT DOCUMENTS

| | | | |
|---|---|---|---|
| 2004/0247550 | A1 | 12/2004 | Asari et al. |
| 2005/0241076 | A1 | 11/2005 | Bureiko |
| 2007/0226916 | A1 | 10/2007 | Mellul et al. |
| 2008/0003192 | A1 | 1/2008 | Modi |
| 2008/0035167 | A1 | 2/2008 | Chan |
| 2009/0048132 | A1 | 2/2009 | Paul |
| 2012/0093900 | A1 | 4/2012 | Khenniche |
| 2013/0209388 | A1 | 8/2013 | Erazo-Majewicz et al. |
| 2014/0116457 | A1* | 5/2014 | Krueger ................. A61Q 5/002 424/70.13 |
| 2015/0239993 | A1 | 8/2015 | Miyoshi et al. |
| 2017/0335242 | A1* | 11/2017 | Eldredge ............... C07C 211/63 |
| 2018/0066212 | A1 | 3/2018 | Pickering et al. |
| 2021/0324303 | A1 | 10/2021 | Partain, III et al. |
| 2022/0040080 | A1 | 2/2022 | Leal et al. |

FOREIGN PATENT DOCUMENTS

| | | | | |
|---|---|---|---|---|
| FR | 2975295 | | 11/2012 | |
| JP | 583278 | B2 | 1/1983 | |
| JP | 2000159642 | | 6/2000 | |
| JP | 2000178303 | | 6/2000 | |
| WO | 2001008644 | | 2/2001 | |
| WO | 2001034103 | | 5/2001 | |
| WO | 2001068040 | | 9/2001 | |
| WO | 2002100360 | | 12/2002 | |
| WO | 2013087286 | | 6/2013 | |
| WO | 2017040876 | A1 | 3/2017 | |
| WO | 2017223246 | A1 | 12/2017 | |
| WO | WO-2018017570 | A1 * | 1/2018 | ............... A61K 8/91 |
| WO | 2019025233 | | 2/2019 | |
| WO | 2019043032 | A1 | 3/2019 | |

* cited by examiner

PROCESS FOR REDUCING HAIR DAMAGE UPON EXPOSURE TO HEAT

The present invention relates to a process for reducing hair damage upon exposure of the hair to heat. In particular, the present invention relates to a process for reducing hair damage upon exposure of the hair to heat, comprising: providing a cosmetically acceptable aqueous carrier; selecting a heat protectant, wherein the heat protectant is selected based on its ability to impart thermal protection to hair from exposure to heat, wherein the heat protectant is selected to be a modified carbohydrate polymer, comprising a cellulose ether base material functionalized with (i) trialkyl ammonium moieties of formula (I)

(I)

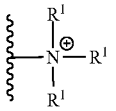

wherein each $R^1$ is independently selected from the group consisting of a $C_{1-7}$ alkyl group and wherein the modified carbohydrate polymer has a Kjeldahl nitrogen content, TKN, corrected for ash and volatiles, of 0.75 to 2.5 wt %; and (ii) hydrophobic substituents each having 16 carbon atoms; wherein the modified carbohydrate polymer comprises 0.005 to 1.5 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons; and wherein the modified carbohydrate polymer comprises <0.001 wt %, based on weight of modified carbohydrate polymer, of crosslinking units; providing the selected heat protectant; combining the cosmetically acceptable aqueous carrier and the heat protectant to form an aqueous thermal protectant formulation; wherein the aqueous thermal protectant formulation contains 0.1 to 5 wt %, based on weight of the aqueous thermal protectant formulation, of the heat protectant; providing a hair; applying the aqueous thermal protectant formulation to the hair; providing a heat generating hair care appliance; and exposing the hair to heat at a temperature of 50 to 300 °C using the heat generating hair care appliance for 1 to 30 minutes.

Heat-assisted processes whereby heat is applied to hair fibers (e.g., during heat-assisted styling or drying using blow dryers, hair straighteners (such as flat irons), curling devices, heated comb, heated brush (with or without a rotating drum) are ubiquitous. Such heat-assisted processes; however, can dry out and damage hair. Moreover, improper technique may lead to damager; such as, for example, holding a blow dryer too close to the hair and overdrying the hair, or by engaging hair with a hot tool for too long at a particular spot of the hair. The heat assisted processes may cause moisture to evaporate or be driven from the hair causing the hair to become brittle and more susceptible to cracking. In addition, heat styling may cause physical damage to the hair. For example, by raising the cuticles and/or creating blisters on individual hair fibers, which may lead to causing increased friction between hair fibers. The increased friction between hair fibers make combing more difficult requiring more force to comb through the hair. The application of increased combing force may in turn wear the outer surface of the hair leading to cracks and breaks in the hair. For many years, researchers believed that human hair would have similar temperature based properties to wool as both are composed of the keratin protein. Recent studies have revealed that human hair exhibits the following characteristics in response to heating. (a) When exposed to heat at ≤150 °C, loosely bound water and tightly bound water is lost or evaporated from the human hair. (b) When exposed to heat at 160 °C to 175 °C, human hair undergoes a glass transition phase; wherein the hair begins to flow as would hot glass. At the glass transition temperature hair may undergo plastic deformation. Normally hydrated hair may elastically stretch and return back to its original length. Hence, normally hydrated hair exhibits temporary plasticity which is why styles like curls, and twist outs/knot outs can occur. However, when treated above the glass transition temperature, the plasticity of hair is not temporary. Upon cooling, the hair may retain the styled, but the hair shaft will have been damaged. (c) When exposed to heat at 215 °C to 235 °C, the keratin, which is present in all hair as a natural alpha helix, melts, thereby permanently damaging the hair. Note that styling of hair is typically done using tools that exhibit operating temperatures in excess of 150 °C to impart style to the hair above the glass transition. When using heat to style hair, the temperature required to exceed the glass transition temperature is proportional to the hydration level of the hair. The higher the moisture content of the hair, the lower the temperature required to reach the glass transition point for the hair. Accordingly, to result in the lowest possible level of undesired damage to the hair, it would be advantageous to maximize the hydration of the hair during the heat assisted styling process.

One process for treating keratin fibers is described by Greaves al. in WO 2019043032. Greaves et al. disclose a process for treating keratin fibers, especially human keratin fibers, in particular the hair, comprising: (i) a step consisting in applying, to said fibers, a) one or more monosaccharides with amine group(s); (ii) a step consisting in applying, to said fibers, b) one or more polysaccharides with amine group(s); (ii') optionally a drying step; (iii) then a step of heat treatment at a temperature above or equal to 80 °C, in particular at a temperature between 100 °C and 250 °C, preferably with a hair iron; it being understood that the steps (i) and (ii) may be carried out simultaneously, or sequentially, preferably the steps (i) and (ii) are carried out simultaneously and that the drying step (ii'), when it is present, precedes the heat treatment step and follows the steps (i) and (ii).

Notwithstanding, there remains a need for processes for reducing hair damage upon exposure of heat to the hair.

The present invention provides a process for reducing hair damage upon exposure of the hair to heat, comprising: providing a cosmetically acceptable aqueous carrier; selecting a heat protectant, wherein the heat protectant is selected based on its ability to impart thermal protection to hair from exposure to heat, comprising a cellulose ether base material functionalized with (i) trialkyl ammonium moieties of formula (I)

(I)

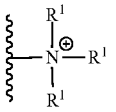

wherein each $R^1$ is independently selected from the group consisting of a $C_{1-7}$ alkyl group and wherein the modified carbohydrate polymer has a Kjeldahl nitrogen content, TKN, corrected for ash and volatiles, of 0.75 to 2.5 wt %; and (ii) hydrophobic substituents each having 16 carbon atoms; wherein the modified carbohydrate polymer comprises 0.005 to 1.5 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons; and wherein the modified carbohydrate polymer comprises <0.001 wt %, based on weight of modified carbohydrate polymer, of crosslinking units; providing the selected heat protectant; combining the cosmetically acceptable aqueous carrier and the heat protectant to form an aqueous thermal protectant formulation; wherein the aqueous thermal protectant formulation contains 0.1 to 5 wt %, based on weight of the aqueous thermal protectant formulation, of the heat protectant; providing a hair; applying the aqueous thermal protectant formulation to the hair; providing a heat generating hair care appliance; and exposing the hair to heat at a temperature of 50 to 300 °C using the heat generating hair care appliance for 1 to 30 minutes.

DETAILED DESCRIPTION

We have surprisingly found that hair treated with an aqueous thermal protectant formulation of the present invention before exposure to heat; wherein the aqueous thermal protection formulation includes a selected heat protectant, wherein the heat protectant is selected based on its ability to impart thermal protection to hair from exposure to heat, wherein the heat protectant is selected to be a modified carbohydrate polymer, comprising a cellulose ether base material functionalized with (i) trialkyl ammonium moieties of formula (I)

(I)

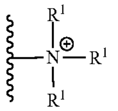

wherein each $R^1$ is independently selected from the group consisting of a $C_{1-7}$ alkyl group and wherein the modified carbohydrate polymer has a Kjeldahl nitrogen content, TKN, corrected for ash and volatiles, of 0.75 to 2.5 wt %; and (ii) hydrophobic substituents each having 16 carbon atoms; wherein the modified carbohydrate polymer comprises 0.005 to 1.5 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons; and wherein the modified carbohydrate polymer comprises <0.001 wt %, based on weight of modified carbohydrate polymer, of crosslinking units; the treated hair exhibits at least one of a higher denaturation temperature than hair similarly exposed to heat but without application of the aqueous protectant formulation and a higher denaturation enthalpy than hair similarly exposed to heat but without application of the aqueous protectant formulation.

Unless otherwise indicated, ratios, percentages, parts, and the like are by weight.

As used herein, unless otherwise indicated, the phrase "molecular weight" or $M_W$ refers to the weight average molecular weight as measured in a conventional manner with gel permeation chromatography (GPC) and conventional standards, such as polyethylene glycol standards. GPC techniques are discussed in detail in Modern Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons, or equivalently, g/mol.

The term "cosmetically acceptable" as used herein and in the appended claims refers to ingredients typically used in personal care compositions, and is intended to underscore that materials that are toxic when present in the amounts typically found in personal care compositions are not contemplated as part of the present invention.

Preferably, the process for reducing hair (preferably, mammalian hair; more preferably, human hair) damage upon exposure of the hair to heat of the present invention, comprises: providing a cosmetically acceptable aqueous carrier; selecting a heat protectant, wherein the heat protectant is selected based on its ability to impart thermal protection to hair from exposure to heat, wherein the heat protectant is selected to be a modified carbohydrate polymer, comprising a cellulose ether base material functionalized with (i) trialkyl ammonium moieties of formula (I)

(I)

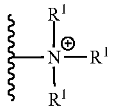

wherein each $R^1$ is independently selected from the group consisting of a $C_{1-7}$ alkyl group (preferably, a $C_{1-4}$ alkyl group; more preferably, a methyl group and an ethyl group; most preferably, a methyl group) and wherein the modified carbohydrate polymer has a Kjeldahl nitrogen content, TKN, corrected for ash and volatiles, of 0.75 to 2.5 wt % (preferably, 0.8 to 2.2 wt %; more preferably, 1.5 to 2.1 wt %; most preferably, 1.7 to 1.9 wt %); and (ii) hydrophobic substituents each having 16 carbon atoms; wherein the modified carbohydrate polymer comprises >0.005 to 1.5 wt % (preferably, 0.1 to 1.1 wt %; more preferably, 0.2 to 0.7; still more preferably, 0.3 to <0.5 wt %; most preferably, 0.4 to 0.46 wt %), based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); and wherein the modified carbohydrate polymer comprises <0.001 wt % (preferably, <0.0001 wt %; more preferably, <0.00001 wt %; most preferably, less than the detectable limit), based on weight of modified carbohydrate polymer, of crosslinking units; providing the selected heat protectant; combining the cosmetically acceptable aqueous carrier and the heat protectant to form an aqueous thermal protectant formulation (preferably, wherein the aqueous thermal protectant formulation comprises 25 to 99.95 wt % (preferably, 50 to 99.9 wt %; more preferably, 75 to 99.5 wt %; most preferably, 80 to 99.3 wt %), based on weight of the aqueous thermal protectant formulation, of the cosmetically acceptable aqueous carrier; and 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of the heat protectant); providing a hair; applying the aqueous thermal protectant formulation to the hair (preferably, applying from 0.01 g to 5 g of the aqueous hair care formulation per g of hair); optionally, rinsing the hair with water (preferably, wherein the hair is rinsed before applying the aqueous protectant formulation to the hair); optionally, drying the rinsed hair by at least one of toweling and pressing hair to remove excess water (preferably, wherein the hair is dried by at least one of toweling and pressing hair to remove excess water before applying the aqueous protectant formulation to the hair); optionally, at least one of combing and brushing the hair following application of the aqueous thermal protectant formulation (preferably, wherein the hair is combed and/or brushed before, during and/or after exposing the hair to heat from the heat generating hair care appliance); providing a heat generating hair care appliance (e.g., flat ironing/curling; setting hair in curlers and heating; curling with a curling iron; and hot rollers)(a hair styling appliance, wherein the hair styling appliance is selected from the group consisting of at least one of a hair dryer, a hot air hair styler and a hair curler); exposing the hair to heat at a temperature of 50 to 300 °C (preferably, 80 to 280 °C; more preferably, 90 to 275 °C; most preferably, 100 to 250 °C) using the heat generating hair care appliance (wherein the heat generating hair care appliance is selected from the group consisting of at least one of a hot air hair care appliance (e.g., hair dryer, hot air hair styler) and a hot surface hair care appliance (e.g., hot curlers, flat iron and a curling iron)) for 1 to 30 minutes (e.g., for drying or styling hair) (preferably, providing a hot air hair care appliance and a hot surface hair care appliance for 1 to 20 minutes for drying the hair followed by treatment of the hair with a hot surface hair care appliance for 1 to 20 minutes for styling the hair)(preferably, wherein the hair to which the aqueous protectant formulation has been applied exhibits at least one of a higher denaturation temperature than hair similarly exposed to heat but without application of the aqueous protectant formulation and a higher denaturation enthalpy than hair similarly exposed to heat but without application of the aqueous protectant formulation) (more preferably, wherein the hair to which the aqueous protectant formulation has been applied exhibits a higher denaturation temperature and a higher denaturation enthalpy than hair similarly exposed to heat but without application of the aqueous protectant formulation).

Preferably, the aqueous thermal protectant formulation prepared and used in the process of the present invention, comprises a cosmetically acceptable aqueous carrier. More preferably, the aqueous thermal protectant formulation provided and used in the process of the present invention, comprises: 25 to 99.95 wt % (preferably, 50 to 99.9 wt %; more preferably, 75 to 99.5 wt %; most preferably, 80 to 99.3 wt %), based on weight of the aqueous thermal protectant formulation, of the cosmetically acceptable aqueous carrier. Most preferably, the aqueous conditioner formulation of the present invention, comprises: 25 to 99.95 wt % (preferably, 50 to 99.9 wt %; more preferably, 75 to 99.5 wt %; most preferably, 80 to 99.3 wt %), based on weight of the aqueous thermal protectant formulation, of the cosmetically acceptable aqueous carrier; wherein the cosmetically acceptable carrier comprises water.

Preferably, the water used in the aqueous thermal protectant formulation prepared and used in the process of the present invention is at least one of distilled water and deionized water. More preferably, the water used in the aqueous thermal protectant formulation prepared and used in the process of the present invention is distilled and deionized.

Preferably, the aqueous thermal protectant formulation prepared and used in the process of the present invention comprises a heat protectant. More preferably, the aqueous thermal protectant formulation prepared and used in the process of the present invention comprises a heat protectant, wherein the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant. Most preferably, the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant; wherein the heat protectant is selected based on its ability to impart thermal protection to hair from exposure to heat and wherein the heat protectant is selected to be a modified carbohydrate polymer, comprising a cellulose ether base material functionalized with (i) trialkyl ammonium moieties of formula (I)

(I)

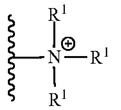

wherein each $R^1$ is independently selected from the group consisting of a $C_{1-7}$ alkyl group (preferably, a $C_{1-4}$ alkyl group; more preferably, a methyl group and an ethyl group; most preferably, a methyl group) and wherein the modified carbohydrate polymer has a Kjeldahl nitrogen content, TKN, corrected for ash and volatiles, of 0.75 to 2.5 wt % (preferably, 0.8 to 2.2 wt %; more preferably, 1.5 to 2.1 wt %; most preferably, 1.7 to 1.9 wt %); and (ii) hydrophobic substituents, wherein the hydrophobic substituents comprise an alkyl group having 16 carbon atoms; wherein the modified carbohydrate polymer comprises >0.005 to 1.5 wt % (preferably, 0.1 to 1.1 wt %; more preferably, 0.2 to 0.7; still more preferably, 0.3 to <0.5 wt %; most preferably, 0.4 to 0.46 wt %), based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); and wherein the modified carbohydrate polymer comprises <0.001 wt % (preferably, <0.0001 wt %; more preferably, <0.00001 wt %; most preferably, less than the detectable limit), based on weight of modified carbohydrate polymer, of crosslinking units.

Preferably, the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons). More preferably, the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); wherein the cellulose ether base material is selected from the group consisting of hydroxyethyl cellulose, hydroxypropyl cellulose, ethyl hydroxyethyl cellulose, methyl cellulose, hydroxypropyl methyl cellulose, hydroxyethyl methyl cellulose and mixtures thereof. Still more preferably, the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); wherein the cellulose ether base material is selected from the group consisting of hydroxyethyl cellulose, hydroxypropyl cellulose and mixtures thereof. Most preferably, the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); wherein the cellulose ether base material is hydroxyethyl cellulose.

Preferably, the aqueous thermal protectant formulation prepared and used in the process of the present invention comprises a heat protectant, wherein the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant; wherein the heat protectant is selected based on its ability to impart thermal protection to hair from exposure to heat and wherein the heat protectant is selected to be a modified carbohydrate polymer, comprising a cellulose ether base material functionalized with (i) trialkyl ammonium moieties of formula (I), wherein each $R^1$ is independently selected from the group consisting of a $C_{1-7}$ alkyl group (preferably, a $C_{1-4}$ alkyl group; more preferably, a methyl group and an ethyl group; most preferably, a methyl group) and wherein the modified carbohydrate polymer has a Kjeldahl nitrogen content corrected for ash and volatiles, TKN, of 0.75 to 2.5 wt % (preferably, 0.8 to 2.2 wt %; more preferably, 1.5 to 2.1 wt %; most preferably, 1.7 to 1.9 wt %). More preferably, the aqueous thermal protectant formulation prepared and used in the process of the present invention comprises a heat protectant, wherein the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant; wherein the heat protectant is selected based on its ability to impart thermal protection to hair from exposure to heat and wherein the heat protectant is selected to be a modified carbohydrate polymer; wherein the modified carbohydrate polymer comprises a cellulose ether base material functionalized with (i) trialkyl ammonium moieties of formula (I), wherein each $R^1$ is independently selected from the group consisting of a $C_{1-7}$ alkyl group (preferably, a $C_{1-4}$ alkyl group; more preferably, a methyl group and an ethyl group; most preferably, a methyl group); wherein the modified carbohydrate polymer has a Kjeldahl nitrogen content corrected for ash and volatiles, TKN, of 0.75 to 2.5 wt % (preferably, 0.8 to 2.2 wt %; more preferably, 1.5 to 2.1 wt %; most preferably, 1.7 to 1.9 wt %); and wherein the modified carbohydrate polymer contains <0.1 moles (preferably, <0.01 moles; more preferably, <0.001 moles; most preferably, less than a detectable limit) of trialkyl ammonium moieties having formal (II) per mole of the cellulose ether base material (II)

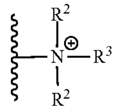

wherein each $R^2$ is independently selected from a methyl group and an ethyl group and wherein $R^3$ is selected from a $C_{8-30}$ alkyl group.

Preferably, the aqueous thermal protectant formulation prepared and used in the process of the present invention comprises a heat protectant, wherein the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant; wherein the heat protectant is selected based on its ability to impart thermal protection to hair from exposure to heat and wherein the heat protectant is selected to be a modified carbohydrate polymer; wherein the modified carbohydrate polymer comprises a cellulose ether base material functionalized with (ii) hydrophobic substituents, wherein the hydrophobic substituents comprise an alkyl group having 16 carbon atoms; wherein the modified carbohydrate polymer comprises >0.005 to 1.5 wt % (preferably, 0.1 to 1.1 wt %; more preferably, 0.2 to 0.7; still more preferably, 0.3 to <0.5 wt %; most preferably, 0.4 to 0.46 wt %), based on weight of the cellulose ether base material, of the hydrophobic substituents. More preferably, the aqueous thermal protectant formulation prepared and used in the process of the present invention comprises a heat protectant, wherein the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant; wherein the heat protectant is selected based on its ability to impart thermal protection to hair from exposure to heat and wherein the heat protectant is selected to be a modified carbohydrate polymer; wherein the modified carbohydrate polymer comprises a cellulose ether base material functionalized with (ii) hydrophobic substituents, wherein the hydrophobic substituents comprise an alkyl group having 16 carbon atoms bonded to the cellulose ether base material through at least one of an ether linkage (e.g., an ether linkage alone or an ether linkage and a 2-hydroxypropyl group) and an ester linkage; wherein the modified carbohydrate polymer comprises >0.005 to 1.5 wt % (preferably, 0.1 to 1.1 wt %; more preferably, 0.2 to 0.7; still more preferably, 0.3 to <0.5 wt %; most preferably, 0.4 to 0.46 wt %), based on weight of the cellulose ether base material, of the hydrophobic substituents. Still more preferably, the aqueous thermal protectant formulation prepared and used in the process of the present invention comprises a heat protectant, wherein the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulalation, of a heat protectant; wherein the heat protectant is selected based on its ability to impart thermal protection to hair from exposure to heat and wherein the heat protectant is selected to be a modified carbohydrate polymer; wherein the modified carbohydrate polymer comprises a cellulose ether base material functionalized with (ii) hydrophobic substituents, wherein the hydrophobic substituents comprise an alkyl group having 16 carbon atoms bonded to the water-soluble cellulose ether base material through at least one of an ether linkage (e.g., an ether linkage alone or an ether linkage and a 2-hydroxypropyl group) and an ester linkage; wherein the modified carbohydrate polymer comprises >0.005 to 1.5 wt % (preferably, 0.1 to 1.1 wt %; more preferably, 0.2 to 0.7; still more preferably, 0.3 to <0.5 wt %; most preferably, 0.4 to 0.46 wt %), based on weight of the cellulose ether base material, of the hydrophobic substituents; and wherein the hydrophobic groups are randomly distributed across the backbone of the cellulose ether base material. Most preferably, the aqueous thermal protectant formulation prepared and used in the process of the present invention comprises a heat protectant, wherein the aqueous thermal protectant formulation prepared and used in the process of the present invention comprises 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of a heat protectant; wherein the heat protectant is selected based on its ability to impart thermal protection to hair from exposure to heat and wherein the heat protectant is selected to be a modified carbohydrate polymer; wherein the modified carbohydrate polymer comprises a cellulose ether base material functionalized with (ii) hydrophobic substituents, wherein the hydrophobic substituents comprise an alkyl group having 16 carbon atoms bonded to the water-soluble cellulose ether base material through at least one of an ether linkage or an ether linkage and a 2-hydroxypropyl group; wherein the modified carbohydrate polymer comprises >0.005 to 1.5 wt % (preferably, 0.1 to 1.1 wt %; more preferably, 0.2 to 0.7; still more preferably, 0.3 to <0.5 wt %; most preferably, 0.4 to 0.46 wt %), based on weight of the cellulose ether base material, of the hydrophobic substituents; and wherein the hydrophobic groups are randomly distributed across the backbone of the cellulose ether base material.

Preferably, the modified carbohydrate polymer is of formula (III)

(III)

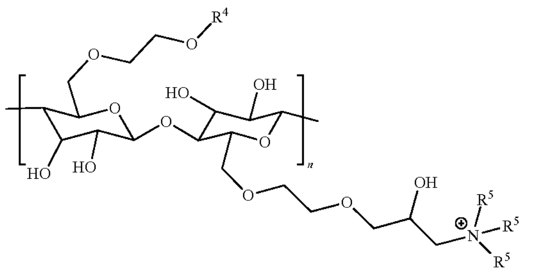

wherein n is determined based on the weight average molecular weight, $M_W$, of the cellulose ether base material; wherein $R^4$ is an alkyl group having 16 carbon atoms and wherein each $R^5$ is independently selected from the group consisting of a $C_{1-7}$ alkyl group (preferably, a $C_{1-4}$ alkyl group; more preferably, a methyl group and an ethyl group; most preferably, a methyl group); and wherein the cellulose ether base material has a weight average molecular weight, $M_W$, of >1,000,000 Daltons (preferably, 1,100,000 to 4,000,000 Daltons; more preferably, 1,200,000 to 2,000,000 Daltons; most preferably, 1,300,000 to 1,800,000 Daltons); and wherein the modified carbohydrate polymer comprises <0.001 wt % (preferably, <0.0001 wt %; more preferably, <0.00001 wt %; most preferably, less than the detectable limit), based on weight of modified carbohydrate polymer, of crosslinking units.

Preferably, the aqueous thermal protectant formulation prepared and used in the process of the present invention is selected from the group consisting of a rinse off hair treatment and a leave in hair treatment. More preferably, the aqueous thermal protectant formulation prepared and used in the process of the present invention is a leave in hair treatment.

Preferably, the aqueous thermal protectant formulation prepared and used in the process of the present invention, optionally, further comprises at least one additional ingredient selected from the group consisting of a cosmetically acceptable cleansing surfactant; a thickener (e.g., polysaccharides, cellulosic polymers); a soap; a colorant; pH adjusting agent; an antioxidant (e.g., butylated hydroxytoluene); an emollient (polyoxyethylene glycol ($C_{7-20}$) fatty acid, esters of glycerol—e.g., PEG-7 glyceryl cocoate, PEG-30 glyceryl cocoate, PEG-12 glyceryl laureate, PEG-20 glyceryl oleate); a wax; a foaming agent; an emulsifying agent (e.g. PEG-100 stearate & glyceryl stearate mixture); a colorant; a fragrance; a chelating agent (e.g., disodium EDTA, tetrasodium EDTA, citric acid, lactic acid); an antimicrobial agent/preservative (e.g., methylchloroisothiazolinone, phenoxyethanol, methylisothiazolinone, esters of parabenzoic acid, diazolidinyl urea and imidazolidinyl urea, benzoic acid, sorbic acid); a bleaching agent; a lubricating agent; a sensory modifier; a sunscreen additive; a vitamin; a protein/amino acid; a plant extract; a natural ingredient; a bioactive agent; an anti-aging agent; a pigment; an acid; a penetrant; an anti-static agent; an anti-frizz agent; an anti-dandruff agent; a hair waving/straightening agent; a hair styling agent; a hair oil; an absorbent; a hard particle; a soft particle; a conditioning agent (e.g., guar hydroxypropyltrimonium chloride, PQ-10, PQ-7); a slip agent; an opacifier; a pearlizing agent and a salt. More preferably, the aqueous thermal protectant formulation prepared and used in the process of the present invention, optionally, further comprises at least one additional ingredient selected from the group consisting of an emulsifying agent (e.g. PEG-100 stearate & glyceryl stearate mixture); an antimicrobial agent/preservative (e.g., methylchloroisothiazolinone, phenoxyethanol, methylisothiazolinone, esters of parabenzoic acid, diazolidinyl urea and imidazolidinyl urea, benzoic acid, sorbic acid); a thickener (e.g., polysaccharides, cellulosic polymers); and a chelating agent (e.g., disodium EDTA, tetrasodium EDTA, citric acid, lactic acid). Most preferably, the aqueous thermal protectant formulation prepared and used in the process of the present invention, optionally, further comprises at least one additional ingredient selected from the group consisting of an emulsifying agent mixture of PEG-100 stearate & glyceryl stearate mixture; a hydroxyethyl cellulose polymer thickener; cetearyl alcohol emollient; tetrasodium ethylene diamine tetraacetic acid chelating agent and a mixture of phenoxyethanol and methylisothiazolinone preservative.

Preferably, the aqueous thermal protectant formulation prepared and used in the process of the present invention, optionally further comprises an emulsifying agent. More preferably, the aqueous thermal protectant formulation prepared and used in the process of the present invention further comprises 0.01 to 80 wt % (more preferably, 0.1 to 5 wt %; still more preferably, 0.5 to 2 wt %, most preferably, 0.75 to 1.25 wt %), based on weight of the aqueous thermal protectant formulation, of an emulsifying agent. Most preferably, the aqueous thermal protectant formulation prepared and used in the process of the present invention further comprises 0.01 to 80 wt % (more preferably, 0.1 to 5 wt %; still more preferably, 0.5 to 2 wt %, most preferably, 0.75 to 1.25 wt %), based on weight of the aqueous thermal protectant formulation, of an emulsifying agent; wherein the aqueous conditioner formulation is selected from the group consisting of a leave on hair conditioner and a rinse off hair conditioner; and wherein the emulsifying agent comprises a mixture of PET-100 stearate and glyceryl stearate.

Preferably, the aqueous thermal protectant formulation prepared and used in the process of the present invention optionally further comprises a thickener. More preferably, the aqueous thermal protectant formulation prepared and used in the process of the present invention further comprises a thickener, wherein the thickener is selected to increase the viscosity of the aqueous conditioner formulation, preferably without substantially modifying the other properties of the personal care composition. Still more preferably, the aqueous thermal protectant formulation prepared and used in the process of the present invention further comprises a thickener, wherein the thickener is selected to increase the viscosity of the personal care composition, preferably without substantially modifying the other properties of the personal care composition and wherein the thickener accounts for 0 to 5.0 wt % (preferably, 0.1 to 5.0 wt %; more preferably, 0.2 to 2.5 wt %; most preferably, 0.5 to 2.0 wt %), based on weight of the aqueous thermal protectant formulation. Preferred thickeners include polysaccharides and cellulosic polymers. Preferably, the thickener is a hydroxyethyl cellulose polymer.

Preferably, the aqueous thermal protectant formulation prepared and used in the process of the present invention optionally further comprises a chelating agent. More preferably, the aqueous thermal protectant formulation prepared and used in the process of the present invention further comprises 0.001 to 0.75 wt % (preferably, 0.03 to 0.25 wt %), based on weight of the aqueous thermal protectant formulation, of a chelating agent, wherein the chelating agent is selected from the group consisting of disodium ethylenediaminetetraacetic acid (EDTA), tetrasodium EDTA, citric acid, lactic acid and mixtures thereof. Most preferably, the aqueous thermal protectant formulation prepared and used in the process of the present invention further comprises 0.001 to 0.75 wt % (preferably, 0.03 to 0.25 wt %), based on weight of the aqueous thermal protectant formulation, of a chelating agent, wherein the chelating agent, wherein the chelating agent includes tetrasodium EDTA.

Preferably, the aqueous thermal protectant formulation prepared and used in the process of the present invention optionally further comprises an antimicrobial agent/preservative. More preferably, the aqueous thermal protectant formulation prepared and used in the process of the present invention further comprises 0.05 to 1.25 wt % (preferably, 0.1 to 1 wt %; more preferably, 0.25 to 0.75 wt %), based on weight of the aqueous thermal protectant formulation, of an antimicrobial agent/preservative; wherein the antimicrobial/preservative is selected from the group consisting of phenoxyethanol, benzoic acid, benzyl alcohol, sodium benzoate, DMDM hydantoin, 2-ethylhexyl glyceryl ether, isothiazolinone (e.g., methylchloroisothiazolinone, methylisothiazolinone) and mixtures thereof. Most preferably, the aqueous thermal protectant formulation prepared and used in the process of the present invention optionally further comprises 0.05 to 1.25 wt % (preferably, 0.1 to 1 wt %; more preferably, 0.25 to 0.75 wt %), based on weight of the aqueous thermal protectant formulation, of an antimicrobial agent/preservative; wherein the antimicrobial/preservative is a mixture of phenoxyethanol and an isothiazolinone (more preferably, wherein the antimicrobial/preservative is a mixture of phenoxyethanol and methylisothiazolinone).

Preferably, the aqueous thermal protectant formulation prepared and used in the process of the present invention contains <detectable limit of monosaccharide having amine groups.

Preferably, the aqueous thermal protectant formulation prepared and used in the process of the present invention contains <detectable limit of $C_{3-5}$ monosaccharide.

Preferably, the aqueous thermal protectant formulation prepared and used in the process of the present invention contains <detectable limit of sugar.

Preferably, the aqueous thermal protectant formulation prepared and used in the process of the present invention contains <detectable limit of soy protein.

Preferably, the aqueous thermal protectant formulation prepared and used in the process of the present invention contains <detectable limit of hydrolyzed silk.

Preferably, the aqueous thermal protectant formulation prepared and used in the process of the present invention contains <detectable limit of sugar.

Preferably, the aqueous thermal protectant formulation prepared and used in the process of the present invention contains <0.1 wt % (preferably, <0.01 wt %; more preferably, <0.001 wt %; most preferably, <detectable limit), of hydrophobically modified poly(acrylamido-N-propyltrimethylammonium chloride.

Preferably, in the process for reducing hair (preferably, mammalian hair; more preferably, human hair) damage upon exposure of the hair to heat of the present invention, the provided heat protectant formulation, the cosmetically acceptable aqueous carrier and any additional ingredients are combined using known processing techniques to provide the aqueous thermal protectant formulation. More preferably, in the process for reducing hair (preferably, mammalian hair; more preferably, human hair) damage upon exposure of the hair to heat of the present invention, the provided heat protectant formulation, the cosmetically acceptable aqueous carrier and any additional ingredients are combined using known processing techniques to provide the aqueous thermal protectant formulation; wherein the aqueous thermal protectant formulation comprises 25 to 99.95 wt % (preferably, 50 to 99.9 wt %; more preferably, 75 to 99.5 wt %; most preferably, 80 to 99.3 wt %), based on weight of the aqueous thermal protectant formulation, of the cosmetically acceptable aqueous carrier; and 0.1 to 5 wt % (preferably, 0.15 to 2.5 wt %; more preferably, 0.2 to 2 wt %; most preferably, 0.25 to 1.5 wt %), based on weight of the aqueous thermal protectant formulation, of the heat protectant.

Preferably, in the process for reducing hair (preferably, mammalian hair; more preferably, human hair) damage upon exposure of the hair to heat of the present invention, the aqueous thermal protectant formulation is applied to the hair using well known techniques. More preferably, in the process for reducing hair (preferably, mammalian hair; more preferably, human hair) damage upon exposure of the hair to heat of the present invention, the aqueous thermal protectant formulation is applied to the hair, wherein 0.01 g to 5 g of the aqueous thermal protectant formulation is applied per g of hair.

Preferably, in the process for reducing hair (preferably, mammalian hair; more preferably, human hair) damage upon exposure of the hair to heat of the present invention, comprises providing a heat generating hair care appliance. Heat generating hair care appliances typically fall into one of two major categories, namely (1) heat generating hair care appliances that are used preferably on wet hair (e.g., hair dryer) and (2) heat generating hair care appliances used preferably on dry hair (e.g., flat ironing/curling; hat rollers).

Heat generating appliances that are designed for and typically used on wet hair are sometimes referred to as hot air hair care appliances. Examples of hot air hair care appliances include hair dryers and hot air hair stylers. The typical hair dryer is designed to direct hot air towards the hair to facilitate drying of the hair. In these hair dryers, the air is directed through appropriate orifices and accelerated by a fan. The air expelled by such hair dryers may be heated, but example, through use of a resistive heater. Hair dryers may incorporate a hood, wherein a major portion of the hair is covered by the hood. Hair dryers typically operate by delivering hot air temperatures of 50 to 100 °C. Hot air stylers typically direct hot air through an attachment designed for combing or otherwise manipulating the hair. Hot air stylers may deliver hot air temperatures of up to 130 °C.

Heat generating appliances that are designed for and typically used on dry hare are sometimes referred to as hot surface hair care appliances. Examples of hot surface hair care appliances may be designed for hair curling and/or hair straightening. Hot surface hair care appliances typically rely on resistive heating wherein heat is transported to the hair via direct contact with the appliance rather than using hot air. The heat transfer is typically effectuated by bringing the hair into contact with a metallic or ceramic surface of the hot surface hair care appliance. Hot surface hair care appliances are typically not used to dry the hair. Rather, hot surface hair care appliances are implemented to change the style of the hair, typically either to produce curls in the hair or to straighten the hair. The surfaces of hot surface hair care appliances designed to contact and transfer heat to hair typically achieve temperatures of 130 to 300 °C.

Preferably, in the process for reducing hair (preferably, mammal hair; more preferably, human hair) damage upon exposure of the hair to heat of the present invention, comprises exposing the hair to heat at a temperature of 50 to 300 °C (preferably, 80 to 280 °C; more preferably, 90 to 275 °C; most preferably, 100 to 250 °C) using the heat generating hair care appliance (wherein the heat generating hair care appliance is selected from the group consisting of at least one of a hot air hair care appliance (e.g., hair dryer, hot air hair styler) and a hot surface hair care appliance (e.g., hot curlers, flat iron and a curling iron)) (e.g., for drying or styling hair). More preferably, in the process for reducing hair (preferably, mammal hair; more preferably, human hair) damage upon exposure of the hair to heat of the present invention, comprises exposing the hair to heat at a temperature of 50 to 300 °C (preferably, 80 to 280 °C; more preferably, 90 to 275 °C; most preferably, 100 to 250 °C) using the heat generating hair care appliance (wherein the heat generating hair care appliance is selected from the group consisting of at least one of a hot air hair care appliance (e.g., hair dryer, hot air hair styler) and a hot surface hair care appliance (e.g., hot curlers, flat iron and a curling iron)) for 1 to 40 minutes (e.g., for drying or styling hair). Most preferably, in the process for reducing hair (preferably, mammal hair; more preferably, human hair) damage upon exposure of the hair to heat of the present invention, comprises exposing the hair to heat at a temperature of 50 to 300 °C (preferably, 80 to 280 °C; more preferably, 90 to 275 °C; most preferably, 100 to 250 °C) using the heat generating hair care appliance (wherein the heat generating hair care appliance is selected from the group consisting of at least one of a hot air hair care appliance (e.g., hair dryer, hot air hair styler) and a hot surface hair care appliance (e.g., hot curlers, flat iron and a curling iron)) for 2 to 40 minutes (e.g., for drying or styling hair); wherein the hair is exposed to heat using a hot air hair care appliance for 1 to 20 minutes for drying the hair; and then wherein the hair is exposed to heat using a hot surface hair care appliance for 1 to 20 minutes for styling the hair.

Preferably, in the process for reducing hair (preferably, mammalian hair; more preferably, human hair) damage upon exposure of the hair to heat of the present invention, optionally further comprises rinsing the hair with water. More preferably, in the process for reducing hair (preferably, mammalian hair; more preferably, human hair) damage upon exposure of the hair to heat of the present invention, optionally further comprises rinsing the hair with water before applying the aqueous protectant formulation to the hair (preferably, wherein the hair is rinsed with water 30 seconds to 20 minutes (more preferably, 30 seconds to 5 minutes)). Most preferably, in the process for reducing hair (preferably, mammalian hair; more preferably, human hair) damage upon exposure of the hair to heat of the present invention, optionally further comprises rinsing the hair with water before applying the aqueous thermal protectant formulation to the hair (preferably, wherein the hair is rinsed with water 30 seconds to 20 minutes (more preferably, 30 seconds to 5 minutes)); and then drying the rinsed hair by at least one of toweling and pressing the hair to remove excess water before applying the aqueous protectant formulation to the hair.

Preferably, in the process for reducing hair (preferably, mammalian hair; more preferably, human hair) damage upon exposure of the hair to heat of the present invention, optionally further comprises at least one of combing and brushing the hair. More preferably, in the process for reducing hair (preferably, mammalian hair; more preferably, human hair) damage upon exposure of the hair to heat of the present invention, optionally further comprises at least one of combing and brushing the hair after application of the aqueous thermal protectant formulation (preferably, wherein the hair is combed and/or brushed before, during and/or after exposing the hair to heat from the heat generating hair care appliance).

Some embodiments of the present invention will now be described in detail in the following Examples.

Example S1: Heat Protectant

A 2,000 mL, three necked, round bottomed flask was charged with hydrophobically modified hydroxyethyl cellulose polymer (hmHEC) (90.20 g, EMBARK™ Rheology Modifier 160 available from The Dow Chemical Company) and a mixture of 2-propanol (673.92 g) and deionized water (120.52 g). The flask was fitted with a stirring paddle and motor, a rubber serum cap, a nitrogen inlet and a Claisen adaptor fitted with a subsurface thermocouple and a Friedrich condenser with a mineral oil bubbler. The thermocouple was connected to a J-KEM controller and heating mantle.

While stirring the flask contents, the flask was slowly purged with nitrogen for one hour to remove any entrained oxygen. A nitrogen flow rate of about 1 bubble per second was used. After the nitrogen purge was completed, a 25% aqueous sodium hydroxide solution (9.60 g) was added to the flask contents through the serum cap using a plastic syringe with continued stirring under nitrogen. The flask contents were then allowed to stir for 30 minutes under nitrogen.

Using a plastic syringe a 70% aqueous glycidyl trimethylammonium chloride (60.48 g, available from QUAB Chemicals under the trade name QUAB® 151) was then added to the flask contents dropwise over a few minutes with stirring under nitrogen. When the addition was complete, the flask contents were stirred for 5 minutes, then heat was applied to the flask contents using the J-KEM controller. The temperature set point was 55 °C, and the flask contents were heated at 55 °C for 1.5 hours while stirring under nitrogen.

The flask contents where then cooled to room temperature while maintaining a positive nitrogen pressure in the flask. The flask contents were then neutralized by adding glacial acetic acid (10.0 g) by syringe. After stirring for 10 minutes, the product heat protectant was recovered by vacuum filtration through a metal fritted Buchner funnel. The heat protectant was washed in the Buchner funnel once each with the following: a mixture of 2-propanol (656 g) and deionized water (144 g); a mixture of 2-propanol (720 g) and deionized water (80 g); and 2-propanol (800 g), 40% glyoxal (1.76 g) and glacial acetic acid (0.60 g). The heat protectant was briefly air dried and dried overnight in vacuo at 50 °C.

The heat protectant was manually ground using a mortar & pestle and screened through a #30 mesh US standard sieve to give 100.22 g of product. The heat protectant had a volatiles content of 4.41%, an ash content of 2.70% (as sodium acetate) and a Kjeldahl nitrogen content of 1.844%.

Comparative Examples C1-C4 and Example 1: Thermal Protection

Heat Damage Procedure

Hair tresses (2 g, Slightly Bleached Caucasian available from International Hair Importers) were wetted for 30 seconds in 37 °C distilled water, then 1.5 g of a 9 wt % sodium laureth sulfate (SLES) solution was massaged into the hair before rinsing with water flowing at 0.4 L/min for 30 seconds; detangled with a brush; and then given a final rinse with water flowing at 0.4 L/min for 10 seconds. The hair tresses where then treated by applying and working into the tress a 100 μL/g of a 1 wt % aqueous treatment solution of the active material noted in TABLE 1 (if any). Before the heat treatment of the hair tresses, the flat iron was preheated to 232 °C. Then the tresses were treated ten times for ten seconds each with the flat iron. After that, the tresses were washed with 9 wt % SLES solution, and this hair tress heat treatment and washing was repeated three times before performing the DSC studies below.

TABLE 1

| Example | Active |
|---|---|
| Comparative Example C1 | None |
| Comparative Example C2 | Hydroxyethylcellulose[1] |
| Comparative Example C3 | Polyquaternium-10[2] |

TABLE 1-continued

| Example | Active |
|---|---|
| Comparative Example C4 | Polyquaternium-67[3] |
| Example 1 | Example S1 |

[1]commercially available from The Dow Chemical Company under tradename CELLOCIZE ™ QP 100MH hydroxyethyl cellulose
[2]commercially available from The Dow Chemical Company under tradename UCARE ™ Polymer JR-30M
[3]commercially available from The Dow Chemical Company under tradename SoftCAT ™ Polymer SX-1300X

DSC Studies

Samples were prepared from the hair tresses treated according to each of Comparative Examples C1-C4 and Example 1 by isolating at least two different locks of hair from each tress and trimming them into small (<2 mm long) pieces using clippers. The entire length of the chosen hair locks was cut up and randomly distributed on weighing paper to average any difference in hair properties along the length of the tress. A 10 mg sample was then taken from each pile of small hair pieces using a tweezers. The samples were placed into separate 40 μL stainless steel pan (Perkin-Elmer part number 0319-0218) and distributed evenly on the bottom of the pan. To each pan was added 30 μL of deionized water using a pipette, which plasticizes the cuticle and lowers the hair denaturation temperature below the decomposition temperature. The pans were then press-sealed with a Viton O-ring and a stainless steel lid and weight for total starting mass. To allow the hair samples to equilibrate in hydration level, the sealed pans were allowed to sit for 12 hours at 25 °C. The hair samples were then analyzed by a Differential Scanning calorimeter (DSC) paired with a Refrigerated Cooling System (RCS90) unit. The hair samples were analyzed by equilibrating at 40 °C then heating the samples to 200 °C at a 10 °C per minute temperature ramp rate. During the analysis, the cell flow rate was 25 mL per minute of nitrogen. Instrumental software (TRIOS) was used to determine both the denaturation temperature and the denaturation enthalpy. The denaturation temperature was determined as the peak temperature of the endothermic transition and the denaturation enthalpy was determined by integrating the endothermic transition. The peak temperature from the respect of DSC curves are reported in TABLE 2. The denaturation enthalpy for the hair samples are also reported in TABLE 2.

TABLE 2

| Example | Peak Temp. (° C.) | Enthalpy (J/g) |
|---|---|---|
| Comparative Example C1 (no heat damage) | 152.56 | 22.06 |
| Comparative Example C1 | 141.99 | 13.21 |
| Comparative Example C2 | 147.65 | 16.71 |
| Comparative Example C3 | 148.54 | 15.76 |
| Comparative Example C4 | 149.30 | 17.05 |
| Example 1 | 150.55 | 18.79 |

We claim:

1. A process for reducing hair damage upon exposure of the hair to heat, comprising:
providing a cosmetically acceptable aqueous carrier;
selecting a heat protectant, wherein the heat protectant is selected based on its ability to impart thermal protection to hair from exposure to heat, wherein the heat protectant is selected to be a modified carbohydrate polymer, comprising a cellulose ether base material functionalized with (i) trialkyl ammonium moieties of formula (I)

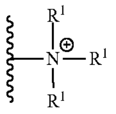

wherein each $R^1$ is independently selected from the group consisting of a $C_{1-4}$ alkyl group and wherein the modified carbohydrate polymer has a Kjeldahl nitrogen content, TKN, corrected for ash and volatiles, of 0.75 to 2.5 wt %; and (ii) hydrophobic substituents each having 16 carbon atoms; wherein the modified carbohydrate polymer comprises 0.005 to 1.5 wt %, based on weight of the cellulose ether base material, of the hydrophobic substituents; wherein the hydrophobic substituents are randomly distributed across the backbone of the cellulose ether base material; wherein the cellulose ether base material has a weight average molecular weight, $M_W$, of >1,000,000 Daltons; and wherein the modified carbohydrate polymer comprises <0.001 wt %, based on weight of modified carbohydrate polymer, of crosslinking units;

providing the selected heat protectant;

combining the cosmetically acceptable aqueous carrier and the heat protectant to form an aqueous thermal protectant formulation; wherein the aqueous thermal protectant formulation contains 0.1 to 5 wt %, based on weight of the aqueous thermal protectant formulation, of the heat protectant;

providing a hair;

applying the aqueous thermal protectant formulation to the hair as a leave in hair treatment;

providing a heat generating hair care appliance; and while the thermal protectant remains on the hair, exposing the hair to heat at a temperature of 50 to 300 °C using the heat generating hair care appliance for 1 to 30 minutes.

2. The process of claim 1, wherein the hair to which the aqueous protectant formulation has been applied exhibits a higher denaturation temperature than hair similarly exposed to heat but without application of the aqueous protectant formulation.

3. The process of claim 2, wherein the hair to which the aqueous protectant formulation has been applied exhibits a higher denaturation enthalpy than hair similarly exposed to heat but without application of the aqueous protectant formulation.

4. The process of claim 3, further comprising: rinsing the hair with water before applying the aqueous thermal protectant formulation to the hair.

5. The process of claim 4, further comprising: drying the rinsed hair by at least one of toweling and pressing hair to remove excess water before applying the aqueous thermal protectant formulation to the hair.

6. The process of claim 3, further comprising: at least one of combing and brushing the hair following application of the aqueous thermal protectant formulation.

7. The process of claim 3, wherein the aqueous protectant formulation applied to the hair, further comprises a thickener.

8. The process of claim 3, wherein the thickener is a polysaccharide.

9. The process of claim 3, wherein the hydrophobic substituent of the selected heat protectant is bonded to the cellulose ether base material through an ether linkage and a 2-hydroxypropyl group.

10. The process of claim 9, wherein the aqueous protectant formulation, further comprises an additive selected from the group consisting of a chelating agent, a preservative, an emollient, a cosmetically acceptable cleansing surfactant and mixtures thereof.

11. The process of claim 1, wherein each $R^1$ is independently selected from the group consisting of a methyl group and an ethyl group.

12. The process of claim 1, wherein each $R^1$ is a methyl group.

13. The process of claim 1, wherein the modified carbohydrate polymer contains <0.001 moles of trialkyl ammonium moieties having formula (II) per mole of the cellulose ether base material

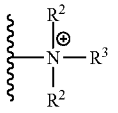

wherein each $R^2$ is independently selected from a methyl group and an ethyl group and wherein $R^3$ is selected from a $C_{8-30}$ alkyl group.

14. The process of claim 1, wherein the modified carbohydrate polymer contains 0 moles of trialkyl ammonium moieties having formula (II) per mole of the cellulose ether base material

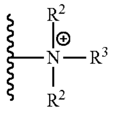

wherein each $R^2$ is independently selected from a methyl group and an ethyl group and wherein $R^3$ is selected from a $C_{6-30}$ alkyl group.

15. The process of claim 1 wherein the modified carbohydrate polymer has the formula (III)

(III)

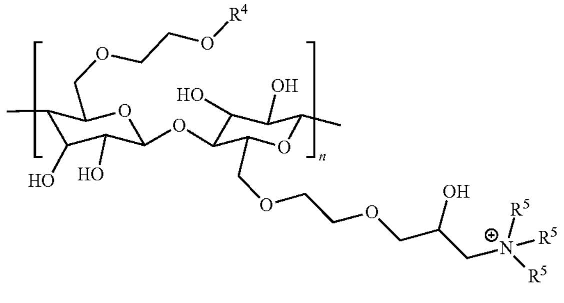

wherein $R^4$ is an alkyl group of 16 carbon atoms, $R^5$ is independently selected from $C_{1-4}$ alkyl group, and n is determined based on the weight average molecular weight.

* * * * *